United States Patent [19]

Brewer, Jr.

[11] Patent Number: 4,795,344
[45] Date of Patent: Jan. 3, 1989

[54] PLAQUE AND CALCULUS REMOVER FOR TISSUE INTEGRATED DENTAL PROSTHESIS

[76] Inventor: Charles A. Brewer, Jr., 105 Via Wazier, Newport Beach, Calif. 92660

[21] Appl. No.: 3,488

[22] Filed: Jan. 15, 1987

[51] Int. Cl.$^4$ .............................................. A61C 17/00
[52] U.S. Cl. .................................. 433/143; 433/141; 433/142
[58] Field of Search ............... 433/143, 144, 141, 142, 433/229; 15/167 R

[56] References Cited

U.S. PATENT DOCUMENTS

| | | | |
|---|---|---|---|
| D. 261,932 | 11/1981 | Bussiere | 433/143 |
| 1,189,505 | 7/1916 | Stockton | 15/167 R |
| 1,397,395 | 11/1921 | Bixler | 433/143 |
| 1,503,610 | 8/1924 | Smith | 433/143 |
| 1,507,500 | 9/1924 | Metz | 15/167 R |
| 1,691,786 | 11/1928 | Roth | 433/143 |
| 1,982,285 | 11/1934 | Bronner | 433/142 |
| 3,742,608 | 7/1973 | Jones | 433/141 |

OTHER PUBLICATIONS

"Screw-In Teeth-the Chic New Dental Trend", by Lance Ignon, 1 page.
"Hygiene Maintenance Procedures for Patients Treated with the Tissue Integrated Prosthesis (Osseointegration)", by Thomas J. Balshi, D.D.S., *Quintessence International*, vol. 17, No. 2/1986, pp. 95-96, 98-100.

*Primary Examiner*—John J. Wilson
*Attorney, Agent, or Firm*—Klein & Szekeres

[57] ABSTRACT

A cleaning instrument for removing plaque and calculus deposits from the titanium anchor cylinders of tissue integrated dental prostheses is disclosed. The instrument, molded from hard plastic, such as polypropylene or glass reinforced nylon, has an elongated handle and a substantially crescent-shaped scraper body disposed at one end of the handle. The scraper body defines an interior opening which is of the same internal diameter as the external diameter of the titanium anchor cylinders to be cleaned. Interior walls of the crescent-shaped scraper have teeth or ridges to provide a scraping or cutting action for the calculus deposits. The crescent-shaped body extends more than one-half of the corresponding circle. Therefore, in order to place the scraper on the titanium cylinder the jaws of the scraper must be slightly spread apart and thereafter the scraper body snaps onto and is removably held on the titanium cylinders. Back and forth rocking action of the instrument then provides good cleaning action of the cylinders.

15 Claims, 2 Drawing Sheets

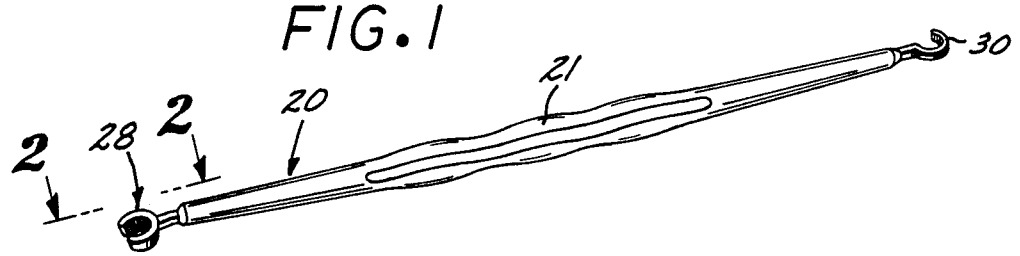
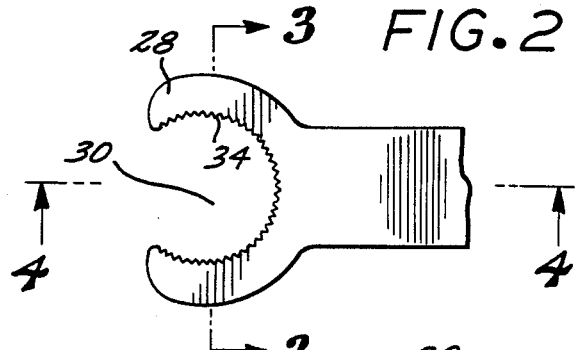
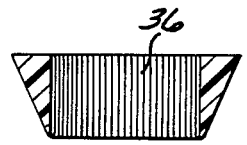
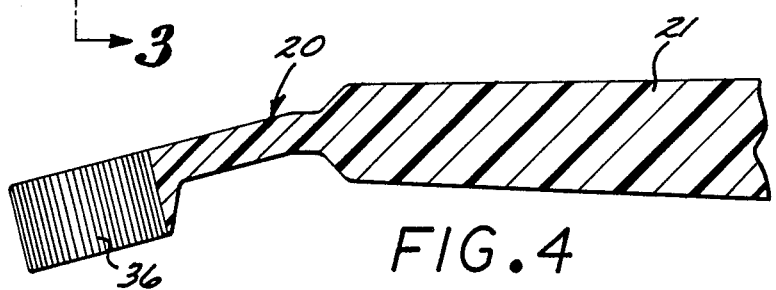
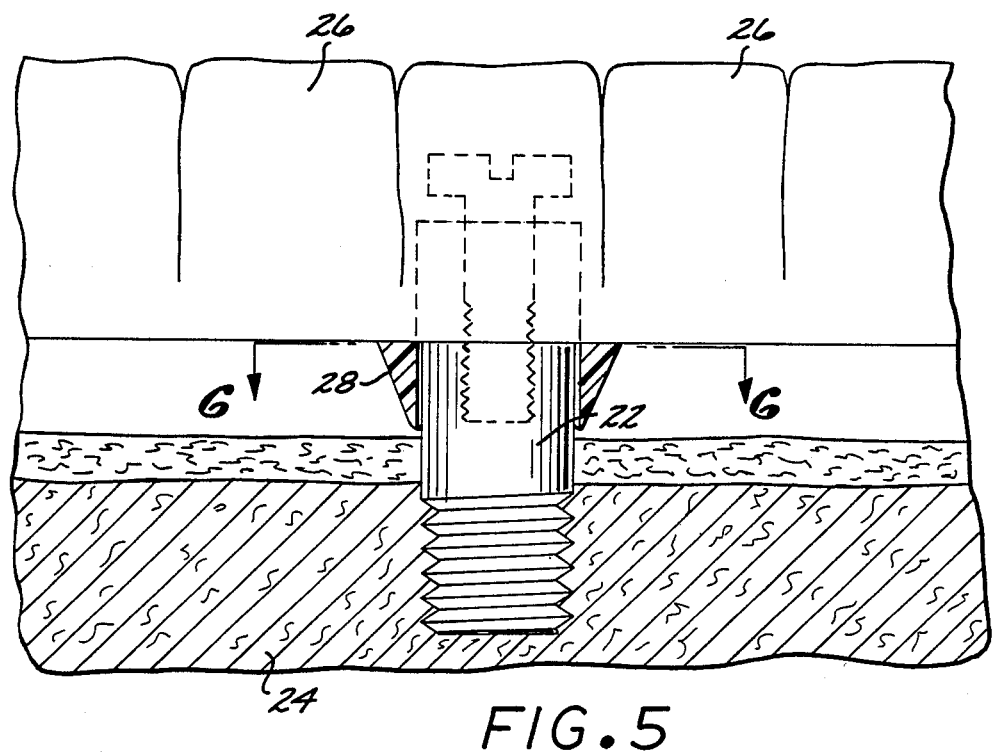

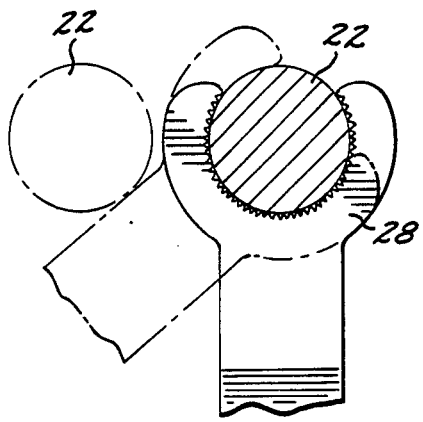
FIG. 6
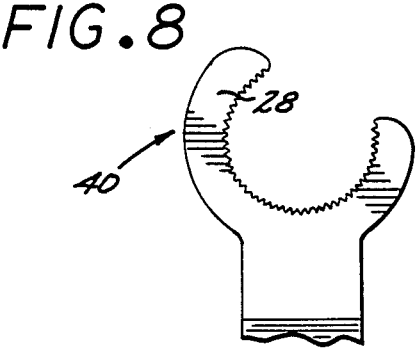
FIG. 8
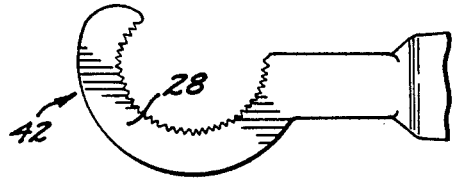
FIG. 9
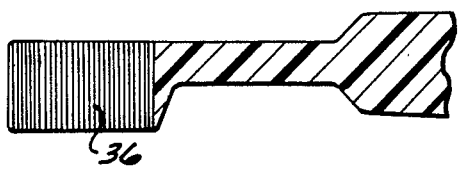
FIG. 10
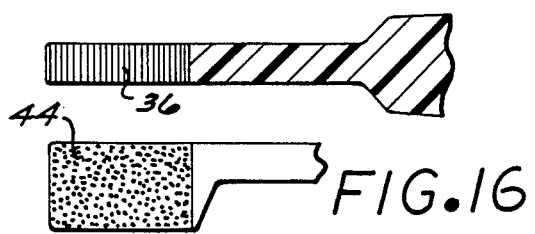
FIG. 11 / FIG. 16
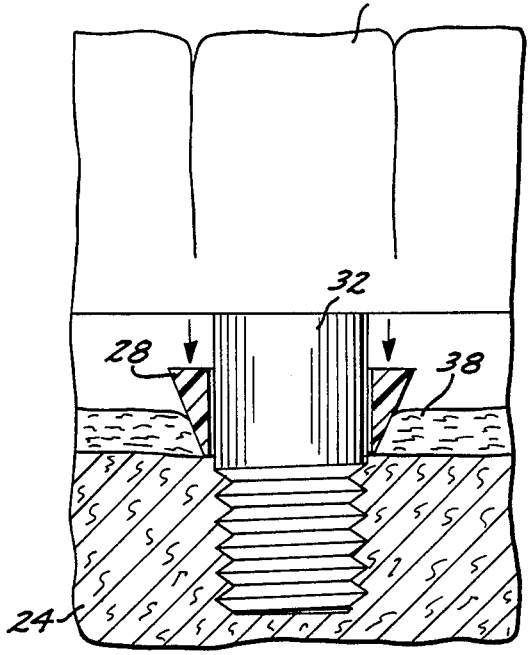
FIG. 7
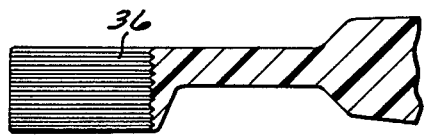
FIG. 12
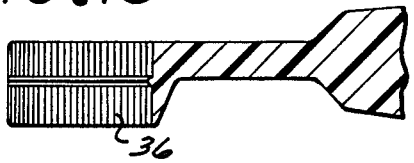
FIG. 13
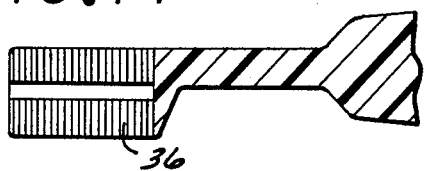
FIG. 14
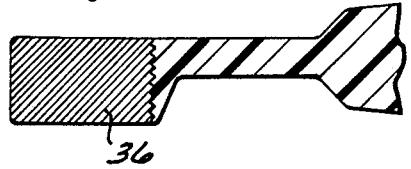
FIG. 15

PLAQUE AND CALCULUS REMOVER FOR TISSUE INTEGRATED DENTAL PROSTHESIS

BACKGROUND OF THE INVENTION

1. Field of the Invention

The present invention is in the field of oral hygiene instruments. More particularly, the present invention is directed to a plaque remover to be used in connection with dental prostheses of the "tissue integrated type", that is, of the type which includes titanium anchor columns directly implanted into the jawbone to support a substructure and a set of artificial teeth.

2. Brief Description of the Prior Art

Dental prostheses have been known for a long time. A relatively recent development in dental prostheses utilizes small titanium cylinders having an outer thread and an inner threaded hole. The titanium cylinders are implanted into tiny holes surgically drilled in the jawbone. After an appropriate healing period, which may be between three to six months, the titanium cylinders are accepted by and firmly anchored in the bone tissue. Then a dental prosthesis including a substructure and a set of artificial teeth is affixed to the titanium support cylinders. The above-summarized dental prosthesis is known in the art as a "tissue integrated prosthesis" and is shown on FIG. 5 of the drawings which are appended to the present patent application.

As is well known in the art, the maintenance of sufficient oral hygiene in connection with dental prosthetic devices is of great importance for health reasons. This is particularly true regarding tissue integrated prostheses, because such prostheses are relatively difficult to keep clean and free of plaque. Moreover, such prosthetic devices are usually provided to persons who already have had significant dental problems and possibly degenerative disease of the gums and/or jawbone.

In connection with the above-summarized tissue integrated prosthesis, it is particularly important to keep those portions of the titanium cylinders plaque and calculus free which extend above the jawbone and through the gums into the oral cavity. As is well known, excessive buildup of plaque and calculus causes gum disease, undesirable recession of the gum line, and degeneration of the jawbone. Moreover, the titanium cylinders are hard to clean, not only because access is relatively difficult, but also because scratching of the metal surface is undesirable in that it causes damage, and scratched surfaces tend to support plaque buildup faster than smooth surfaces.

The prior art has attempted to solve the above-noted problems by providing a specialized instrument having a hook and a crescent-shaped blade. The hooked portion has internal teeth to facilitate removal of calculus deposits. The instrument is made from hard plastic which is adequate to remove calculus but not hard enough to scratch the titanium columns.

In spite of the above-noted specialized tool, there still is need in the prior art for better instruments to clean the titanium anchor columns of tissue integrated prostheses. The present invention provides such a better instrument.

SUMMARY OF THE INVENTION

It is an object of the present invention to provide an improved specialized instrument for cleansing of plaque and calculus deposits from the titanium anchor cylinders of tissue integrated prostheses.

The foregoing and other objects and advantages are attained by an instrument having an elongated handle and a substantially crescent-shaped body at one of its ends. The crescent-shaped body has a hollow circular interior of the same internal diameter as the anchor cylinders of the tissue integrated prosthesis. The interior wall of the abrade calculus or plaque deposits. The crescent-shaped body is configured to extend more than one-half of the diameter of the corresponding circle, whereby it can snap on the titanium cylinders for the cleansing and abrading action.

The features of the present invention can be best understood, together with further objects and advantages, by reference to the following description, taken in connection with the accompanying drawings, wherein like numerals indicate like parts.

BRIEF DESCRIPTION OF THE DRAWINGS

FIG. 1 is a perspective view of the specialized plaque removing instrument of the present invention;

FIG. 2 is an enlarged view showing one end of the instrument;

FIG. 3 is a cross-sectional view, the cross-section taken on lines 3,3 of FIG. 2;

FIG. 4 is another cross-sectional view, the cross-section being taken on lines 4,4 of FIG. 3;

FIG. 5 is a schematic view showing a tissue integrated dental prostheses and the plaque removing instrument in use;

FIG. 6 is a cross-sectional view taken on lines 6,6 of FIG. 5;

FIG. 7 is another schematic view showing a tissue integrated dental prostheses and the plaque removing instrument in use;

FIG. 8 is a partial top view of a second preferred embodiment of the specialized plaque removing instrument of the present invention;

FIG. 9 is a partial top view of a third preferred embodiment of the specialized plaque removing instrument the present invention;

FIG. 10 is a cross-sectional view, the cross-section being taken on lines 10,10 of FIG. 9;

FIGS. 11 through 16 are cross-sectional views, similar to the cross-sectional views of FIG. 10, the views showing several possible configurations of the rough abrasive surface of the crescent-shaped member of the plaque removing instrument of the present invention.

DESCRIPTION OF THE PREFERRED EMBODIMENTS

The following specification taken in conjunction with the drawings sets forth the preferred embodiments of the present invention The embodiments of the invention disclosed herein are the best modes contemplated by the inventor for carrying out his invention in a commercial environment, although it should be understood that several modifications can be accomplished within the parameters of the present invention.

Referring now to FIGS. 1 through 7 of the appended drawings, a first preferred embodiment 20 of the specialized plaque and calculus removing instrument of the present invention is disclosed. As it was noted in the introductory section of the present application for patent, the instrument 20 of the present invention is designed to facilitate oral hygiene of persons having tissue integrated dental prosthesis of the type which has small titanium cylinders 22 implanted in the jawbone 24 to support the false teeth 26 of the prosthesis. This type of tissue integrated dental prosthesis is shown on FIGS. 5 and 7, although the prosthesis itself forms no part of the present invention.

The instrument 20 comprises an elongated member or rod 21 which has a crescent-shaped scraper or cleaning body 28 at one end, whereas the other end terminates in a hook-like member 30. The crescent-shaped scraper member 28 defines a circular opening or hole 32, the internal diameter of which is substantially equal to the diameter of the titanium anchor cylinders 22. The internal wall 34 of the scraper member 28 has a plurality of parallel disposed teeth or ridges 36 which facilitate the scraping action to remove plaque and calculus deposits from the titanium cylinders 22.

A principal novel feature of the present invention is that the crescent-shaped scraper member 28 extends around more than one-half of the circle or hole 32 defined by the scraper 28, so that the scraper "snaps on" and is held on the titanium cylinders 22 when the instrument 20 is used. Stated in other words, the scraper body 28 extends over more than one-half of the circumference of the titanium cylinders 22; therefore, in order to place the scraper 28 on the cylinder 22, the jaws of the scraper 28 must be spread slightly apart and then "snap on" the cylinder 22 to capture the same. The plastic material from which the instrument is made is sufficiently elastic to permit the slight spreading of the jaws of the scraper member 28 and subsequent return to their original shape to capture the cylinder 22.

The above-described ability of the be snapped on and held on the titanium cylinders 22 coupled with subsequent back and forth rocking motion permits thorough cleansing of the cylinders from plaque (not shown) and accumulated calculus (not shown).

The schematic view of FIG. 5 illustrates the scraper body 28 in a position set on, or "snapped onto" one titanium cylinder 22 of the tissue integrated dental prosthesis. FIGS. 3 and 4 show scraping ridges or teeth 36 disposed on the internal walls 34 of the scraper member 28. FIG. 5 above the gums 38. The back and forth rocking action of the instrument 20 is schematically shown on FIG. 6. Because the scraper extends to more than one-half around the circumference of the cylinders 22, the back and forth rocking action is capable of reaching the entire circumference of the cylinder 22, and therefore cleans the cylinder 22 well. This should also be readily apparent from an inspection of the drawings. FIG. 7 shows the scraper 28 disposed partly below the gums 38, in a position which can be reached by the back and forth rocking action while the wedge-shaped scraper body 28 slightly spreads the gums 38. In this regard it is noted that removal of plaque and calculus from the area just below the gums 38 is considered particularly important in order to avoid degenerative gum and bone disease of the oral cavity. The cleansing action of the instrument 20 of the present invention is in sharp contrast with the instruments of the prior art, which permitted only up-and-down scraping action while the instrument had to be manually held against the titanium cylinders 22.

FIG. 8 illustrates a second preferred embodiment 40 of the instrument of the present invention. As is apparent from the drawings, this embodiment 40 differs from the first preferred embodiment 22 in the configuration of the scraper body 28. However, in the second preferred embodiment 40 also, the scraper body 28 encloses more than one-half of the circular interior opening, and therefore extends more than one-half about the circumference of the titanium cylinders 22.

FIG. 9 illustrates a third preferred embodiment 42 of the instrument of the present invention. This embodiment 42 has a substantially hook-shaped scraper body 28, which nevertheless, in accordance with the present invention, extends to more than one-half of a circle.

FIGS. 10 through 15 illustrate several possible configurations for the scraping ridges or teeth 36 disposed the internal wall 34 of the scraper body 28. FIG. 16 shows an internal wall 34 which, instead of teeth or ridges, has a rough sandpaper-like surface 44.

The instrument of the present invention may contain a different type of scraper body 28 at each end of the rod 21. Alternatively, as in the first preferred embodiment 20 shown on FIG. 1, one end of the rod 21 has a scraper body 28 constructed in accordance with the present invention, whereas the other end of the rod 21 simply has a hook-shaped member constructed in accordance with the prior art.

The instrument of the present invention is advantageously injection molded from suitable plastic materials, such as nylon, glass reinforced nylon, or polypropylene.

Several modifications of the present invention may become readily apparent to those skilled in the art in light of the foregoing disclosure. Therefore, the scope of the following claims as such claims are read in light of the disclosure.

What is claimed is:

1. A plaque remover for a tissue integrated dental prosthesis of the type which includes titanium anchor cylinders anchored into the jawbone to support artificial teeth, the plaque remover comprising:
    an elongated handle, and
    a cleaning member located substantially at one end of the handle, the cleaning member being subtantially crescent-shaped, having a hollow substantially circular interior, the internal diameter of which is substantially the same as the external diameter of the anchor cylinders of the prosthesis, the cleaning member extending more than one-half but less than fully about the circumference of other interior whereby the cleaning member extends more than one-half about the circumference of the anchor cylinders, the interior wall of the cleaning member having a rough surface, said crescent-shaped cleaning member being elastic whereby the cleaning member is capable of spreading and snapping on the anchor cylinders of the prosthesis, and because of the abrasive action of its rough surface, it is capable of removing plaque and calculus deposits as the plaque remover is rocked back and forth while held onto the anchor cylinders.

2. The plaque remover of claim 1 wherein the entire plaque remover is injection molded as a unitary piece of material.

3. The plaque remover of claim 1 wherein the rough surface comprises a plurality of ridges.

4. The plaque remover of claim 1 made from a material selected from the group consisting of nylon, polypropylene, and glass-filled nylon.

5. The plaque remover of claim 1 wherein the ridges are aligned in a direction which is at right angles to the plane of the crescent-shaped cleaning member.

6. A manual plaque remover for a tissue integrated dental prosthesis of the type which includes titanium anchor cylinders anchored into the jawbone to support artificial teeth, the plaque remover comprising:

an elongated handle, and a scraper member having a substantially circular opening at one end of the handle, the scraper member forming a wall around said opening such that more than one-half of the circular opening is surrounded by the wall, the wall having ridges comprising scraping teeth and the circular opening being dimensioned so as to fit tightly on the titanium anchor cylinders, and so that when the scraper member surrounds more than one-half of the circumference of the respective cylinder, said scraper member being elastic whereby the scraper member is capable of spreading and snapping on and being removably attached to the titanium cylinders and capable of scraping plaque and calculus deposits off of such cylinders.

7. The plaque remover of claim 6 consisting of a single unitary injection molded body.

8. The plaque remover of claim 7 made from a material selected from a group consisting of nylon, polypropylene, and glass reinforced nylon.

9. The plaque remover of claim 6 being injection molded from polypropylene.

10. The plaque remover of claim 6 wherein the scraper member is a crescent-shaped member.

11. An injection molded plaque remover of unitary construction for a tissue integrated dental prosthesis of the type which includes titanium anchor cylinders anchored into the jawbone to support artificial teeth, the plaque remover comprising:

an elongated plastic handle, and a crescent-shaped member attached to one end of the plastic handle, the crescent-shaped member forming a substantially circular hole of substantially the same diameter as the titanium anchor cylinders, the crescent-shaped member partially surrounding the hole with its internal wall so that more than one-half of the circumference of the hole is formed by the crescent-shaped member, said crescent-shaped member being elastic whereby the crescent-shaped member is capable of spreading and snapping on the anchor cylinders, whereby when the crescent-shaped member is snapped on the anchor cylinders more than one-half of the circumference of the cylinders is covered by the crescent shaped member, and whereby when the crescent shaped member is snapped on a respective anchor cylinder a back and forth rocking motion of the plaque remover causes the crescent shaped member to scrape plaque from the circumference of the respective cylinder.

12. The plaque remover of claim 11 wherein the internal wall of the crescent-shaped member has a plurality of parallel disposed ridges for scraping plaque of the anchor cylinders.

13. The plaque remover of claim 12 wherein the ridges are disposed in a direction transverse to the plane of the crescent-shaped member.

14. The plaque remover of claim 13 wherein the plaque remover is made by injection molding a material selected from a group consisting of nylon, glass reinforced nylon, and polypropylene.

15. The plaque remover is claim 14 wherein the crescent-shaped member is approximately 1/16" to ⅛" wide in the direction perpendicular to the longitudinal axis of the handle.

* * * * *

UNITED STATES PATENT AND TRADEMARK OFFICE
CERTIFICATE OF CORRECTION

PATENT NO. : 4,795,344

DATED : January 3, 1989

INVENTOR(S) : Charles A. Brewer, Jr.

It is certified that error appears in the above-identified patent and that said Letters Patent is hereby corrected as shown below:

Column 2, line 9, after "the", first occurrence, insert

--crescent-shaped body has a rough surface enabling it to--;

Column 2, line 41, after "instrument" insert --of--;

Column 3, line 32, after "the" insert --scraper member 28 to--;

Column 3, line 42, after "Fig.5" insert --illustrates a position of the scraper 28 on the cylinders--;

Column 4, line 29, after "the" insert --present invention should be interpreted solely from the--; and Column 5, line 12, after member insert --is fitted on a respective cylinder, the scraper member--.

Signed and Sealed this

Seventeenth Day of April, 1990

Attest:

HARRY F. MANBECK, JR.

Attesting Officer

Commissioner of Patents and Trademarks